United States Patent [19]
Gotoh

[11] Patent Number: 6,110,679
[45] Date of Patent: Aug. 29, 2000

[54] AGENTS AND A METHOD OF CHROMOSOME PREPARATION USING PROTEIN PHOSPHATASE INHIBITORS INDUCED PREMATURE CHROMOSOME CONDENSATION (PCC) TECHNIQUE

[76] Inventor: Eisuke Gotoh, 143-13 Wakamatsu, Abiko-shi, Chiba-ken, Japan

[21] Appl. No.: 09/079,386

[22] Filed: May 15, 1998

Related U.S. Application Data

[62] Division of application No. 08/514,727, Aug. 14, 1995, Pat. No. 5,789,164.

[30] Foreign Application Priority Data

Aug. 12, 1994 [JP] Japan .................................. 6-210719
Aug. 3, 1995 [JP] Japan .................................. 7-216495

[51] Int. Cl.⁷ .................................................. C12Q 1/68
[52] U.S. Cl. .............................................. 435/6; 435/375
[58] Field of Search ...................... 435/6, 375, 2

[56] References Cited

U.S. PATENT DOCUMENTS 5,480,772  1/1996  Wangh ........................ 435/2

OTHER PUBLICATIONS

Chambers et al. Int. J. Cancer. Vol. 53, pp. 323–327, Jan. 1993.
Tosuji et al. Proc. Natl. Acad. Sci., USA. Vol. 89, pp. 10613–10617, Nov. 1992.
Tosuji et al. Cell Structure and Function. Vol. 18, No. 6, p. 621, Dec. 1993.
Chemical Abstracts, vol. 118, No. 25, p. 327, Jun. 21, 1993, AN–249647, A.P. Dyban et al, "Okadai Acid Induces premature Chromosome Condensation Reflecting the Cell Cycle progression in One–Cell Stage Mouse Embryos", & Mol. Reprod. Dev., vol. 34, No. 4, pp. 402–414, 1993.
Proceedings of the National Academy of Sciences of USA, vol. 88, pp 6843–6847, Aug. 1991, K.E. Steinmann et al. "Chemically Induced premature Mitosis: Differential Response in Rodent and Human Cells and the Relationship to Cyclin B Synthesis and p34(cdc2)/Cyclin B Complex Formation".
EMBO Journal, vol. 9, No. 13, pp. 4331–4338, 1990, K. Yamashita et al, "Okadaic Acid, A Potent Inhibitor Type 1 and Type 2A protein Phosphatases, Activates cdc2/H1 Kinase and Transiently Induces a premature Mitosis–Like State in BHK21 Cells".
Nature, vol. 226, pp. 717–722, May 23, R. T Johnson et al, "Mammalian Cell Fusion: Induction of premature Chromosome Condensation in Interphase Nuclei".
Ishida, Y., 1992, Journal of Cellular physiology, vol. 150, pp. 484–492, 1992.

*Primary Examiner*—Remy Yucel
*Attorney, Agent, or Firm*—Oblon, Spivak, McClelland, Maier & Neustadt, P.C.

[57] ABSTRACT

Agents and a method for generating chromosomes by premature chromosome condensation (PCC) technique utilizes inhibitors of serine/threonine protein phosphatases. When the cells were treated with these agents, they underwent PCC at any phase of cell cycle within 2 hours. This method enables to obtain not only chromosome of mitotic cells but also those from interphase nuclei much easily, quickly and effectively.

12 Claims, 7 Drawing Sheets

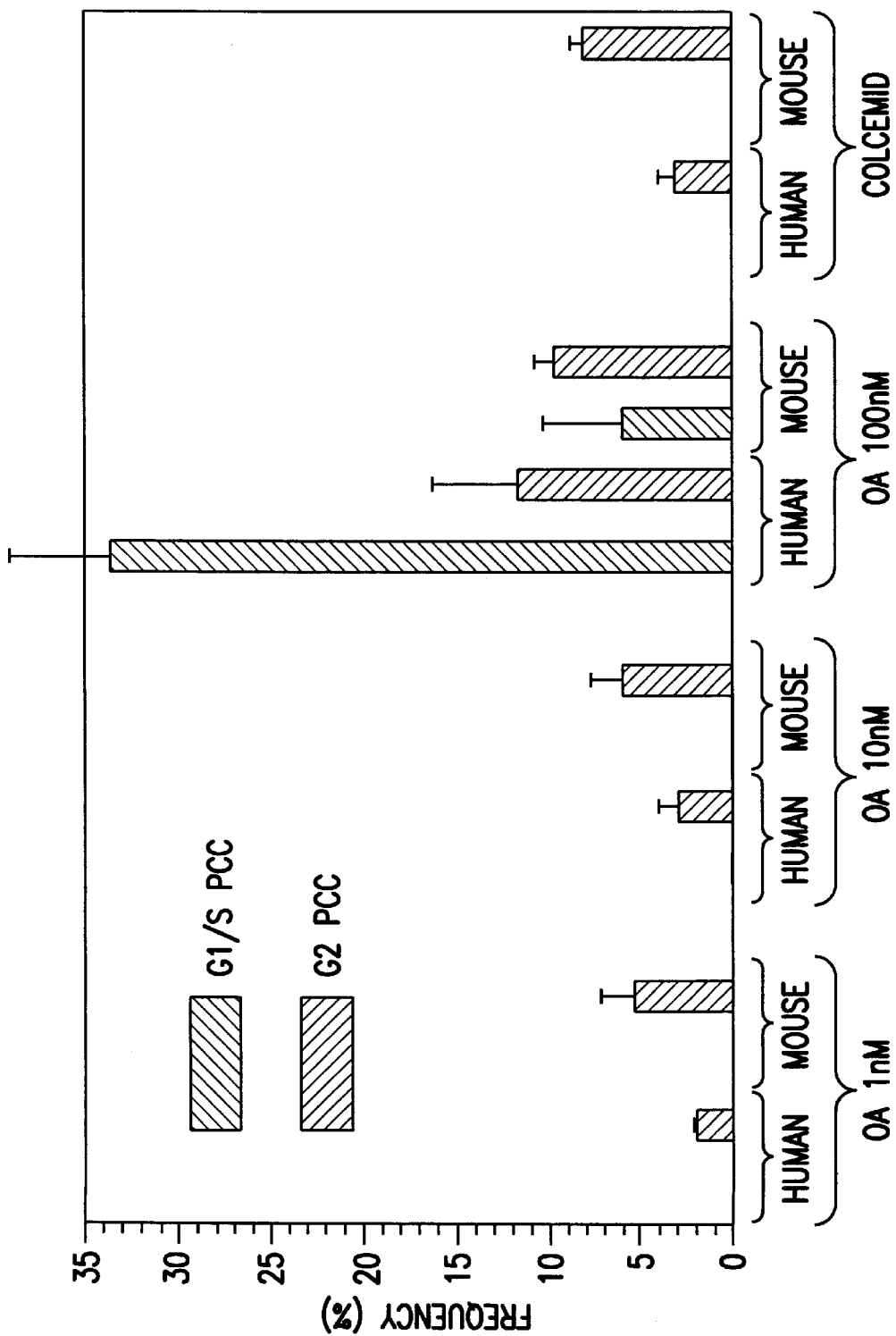

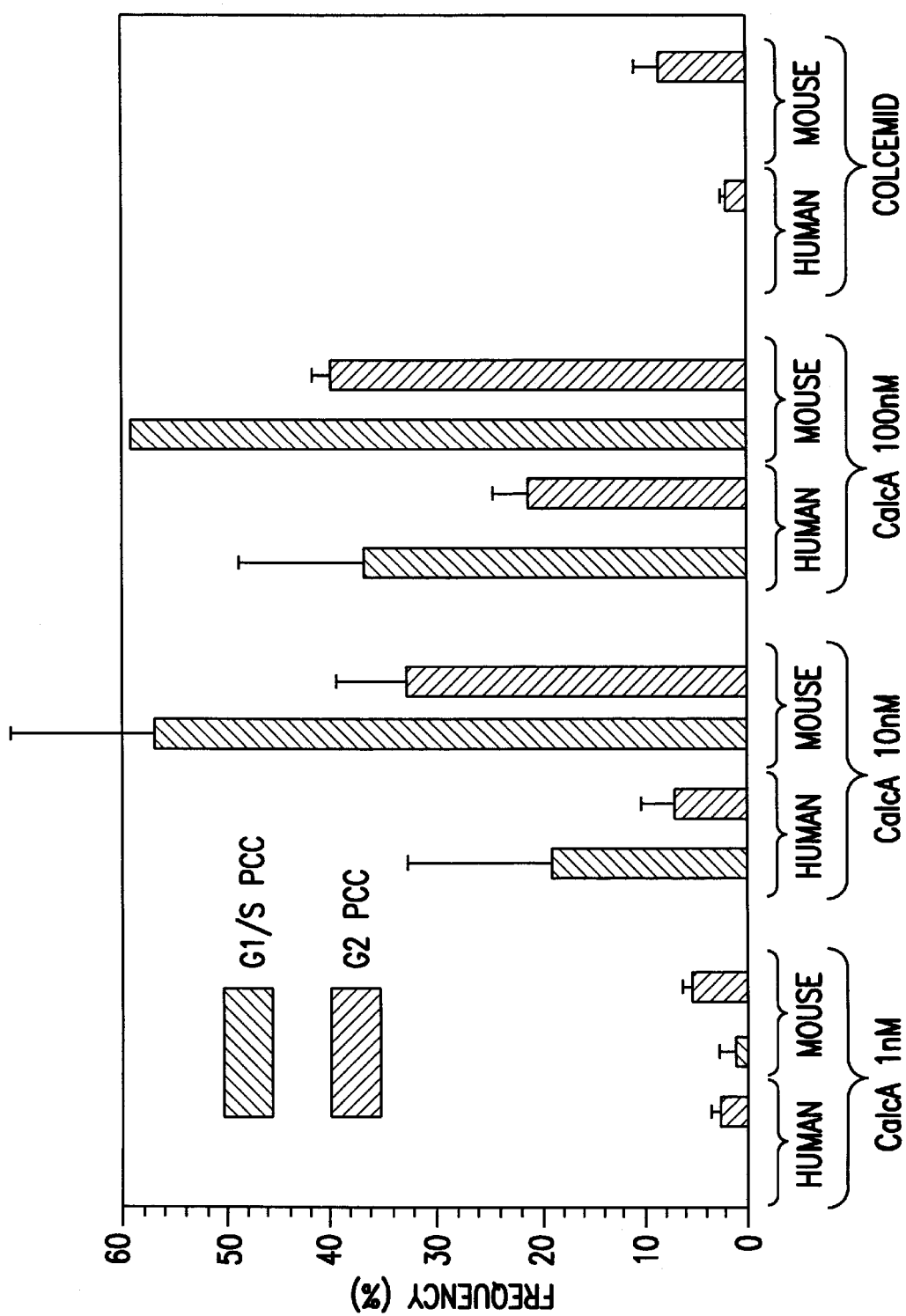

AGENTS AND A METHOD OF CHROMOSOME PREPARATION USING PROTEIN PHOSPHATASE INHIBITORS INDUCED PREMATURE CHROMOSOME CONDENSATION (PCC) TECHNIQUE

This application is a Divisional of application Ser. No. 08/514,727, filed on Aug. 14, 1995, now U.S. Pat. No. 5,789,164.

BACKGROUND OF THE INVENTION

1. Field of the Invention

The present invention relates to the method of obtaining the chromosomes more easily and efficiently than the conventional method using colhitin or its derivatives (colcemid), in more particular to the method of inducing premature chromosome condensation in interphase cell with inhibitors of serine/threonine protein phosphatases, that permit one to obtain not only mitotic chromosomes but also prematurely condensed chromosomes of interphase nuclei.

2. Description of the Related Art

Chromosomal analysis is being widely used for screening or diagnosis of genetic diseases, assay of the mutagenecity of physical or chemical factors or other various cytogenetical purposes in medical, biological, agricultural or other fields. Chromosomes are obtained usually from mitotic cells using colhitin or its derivative, colcemid, thereby inhibiting the assembly of tubulin to form mitotic spindles during mitotic process. Therefore it requires cells to pass through the mitosis. However, it is well known by those skilled in the art, that it is often difficult to obtain chromosomes in the case in which cells are not proliferate well.

Furthermore, many phenomena occur during interphase; for example, chromosomal cleavage by irradiation and subsequent reunion occur through the interphase nuclei, resulting in chromosomal aberration. So it has been required to establish the technique that allows one to obtain chromosomes from interphase cells.

The first approach was done by Johnson and Rao (Johnson and Rao, 1970, *Nature* 226:717). They fused interphase cell in mitotic cell, resulted in the interphase chromosomes condense prematurely (Premature Chromosome Condensation; PCC). However, this method of inducing PCC is technically demanding; synchronizing and collecting large amounts of mitotic cells followed by fusion with target cells. In addition, mixture of chromosomes of interphase and mitotic cell makes it often difficult to analyses the chromosomes of interphase cells.

A similar premature chromosome condensation can be induced by caffeine in cells blocked in S-phase (Schlegel and Pardee, 1986, *Science:*232, 1264). More recently, okadaic acid has also been reported to induce PCC in cells blocked in S-phase (Ghosh et al., 1992, *Exp. Cell Res.:*201, 535, Steinmann et al., 1991, *Proc. Natl. Acad. Sci. USA:*88, 6843, Yamashita et al., 1990, *EMBO J.:*9, 4331). However, the requirement of block the cells in S-phase has limited the use of PCC technique for the analysis of chromosomes.

SUMMARY OF THE INVENTION

The present invention has been proposed in view of the above-mentioned drawbacks inherent to the prior art, and accordingly, one object of the present invention is to provide an improved PCC technique for obtaining chromosomes prematurely from the interphase cells at any time of cell cycle, with quickly, easily, efficiently and in a highly reproducible manner.

According to the present invention, protein phosphatase inhibitors, okadaic acid, okadaic acid ammonium salt, 35-methyl okadaic acid, calyculin A, tautomycin, cantharidine, cantharidic acid and endothal can directly induce PCC in mammalian somatic cells at any time of cell cycles without the block of cells in S-phase. When the cells were treated with these agents, the cells underwent PCC within 2 hour after exposure to these agents. The frequency of PCC obtained by treatment of these agents surpassed that of metaphase chromosomes using colcemid.

These findings indicate that the method, described here, generates the PCC using protein phosphatase inhibitors might take the place of conventional way of obtaining chromosomes using colcemid. Furthermore, this method might permit one to analyze many of the phenomena occurring in interphase nuclei.

BRIEF DESCRIPTION OF THE DRAWINGS

The foregoing and other objects, features and attendant advantages of the present invention will be appreciated as the same become well understood by reviewing description and accompanying drawings wherein:

FIG. 6 shows the dose responsiveness of PCC induced by okadaic acid; shown in Table 1.

FIG. 7 shows the dose responsiveness of PCC induced by calyculin A; shown in Table 2.

As used herein "PCC", refers to an abbreviation of premature chromosome condensation. Because, chromosomes usually condense during mitosis except under certain circumstances. When the chromosomes condense prior to mitosis, this phenomenon is known as premature chromosome condensation. Prematurely condensed chromosomes also give the same abbreviation "PCC". So said "PCC" means both a phenomenon on chromosomes and a condition of those. In many cases, its meanings are interchangeable. Therefore, we use the term "PCC" for both meanings for a phenomenon and a condition of chromosomes, so far not specified.

Prematurely condensed chromosomes or metaphase chromosomes in all the experiment of the present invention were prepared by the usual method which is well known by the skilled in the art. Namely, cells were grown exponentially at 37° C. in 5% $CO_2$ atmosphere under 95% humidity. After treatment of cells with individual agent for up to 2 hours, cells were harvested. Then cells were subjected to hypotonic treatment in 75 mM KCl at 37° C. for 20 minutes to swell the cells. Cells were then fixed with a fixative (3:1 vol./vol. methanol:acetic acid) and then they are spread on a glass slide.

DESCRIPTION OF PREFERRED EMBODIMENTS

Figure 1:
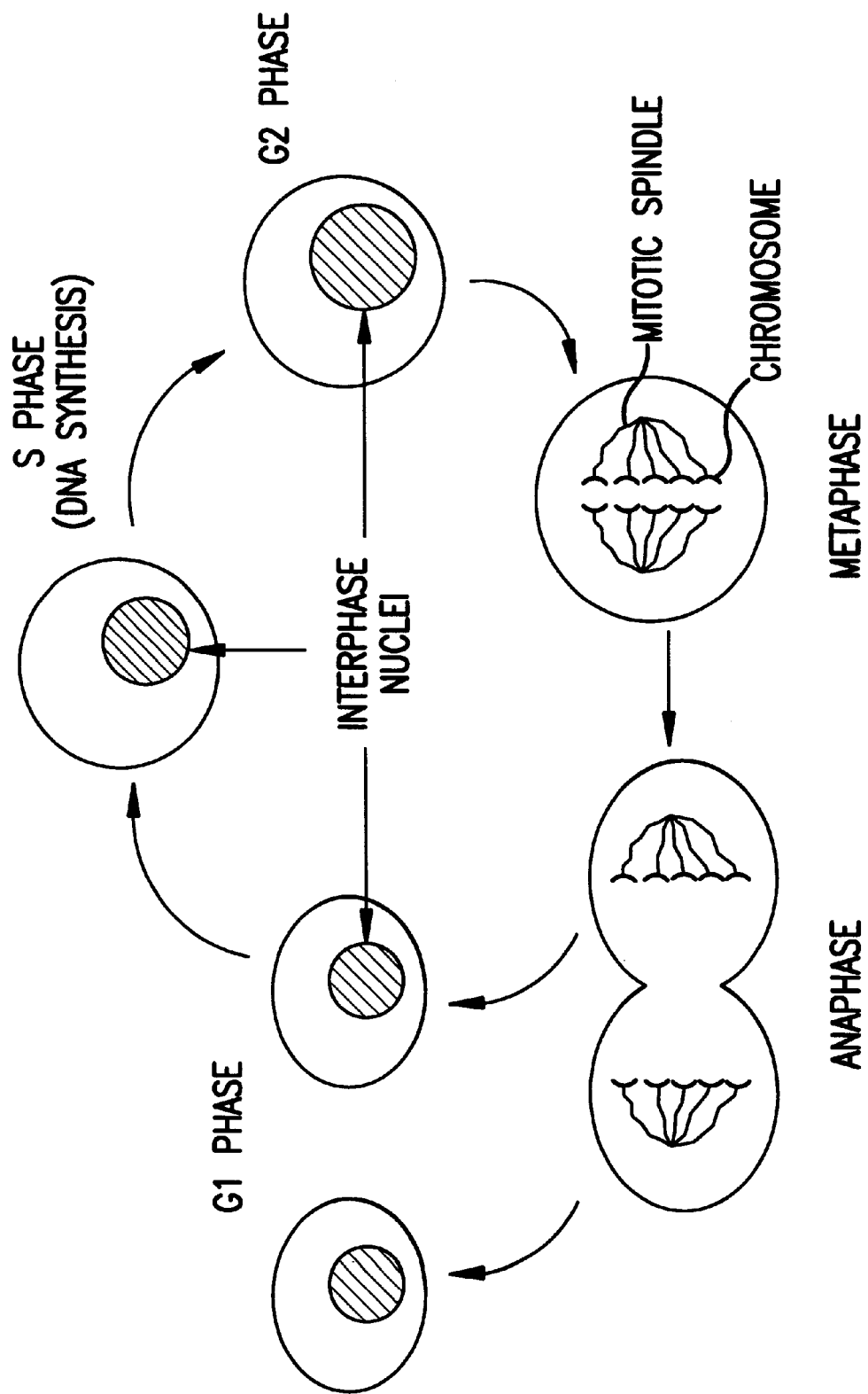
FIG. 1 illustrates the relationship of cell cycle and chromosome condensation.

Referring now to FIG. 1 which illustrates the relationship between cell cycle and chromosome condensation. The cells proliferate through the $G_1$ (Gap 1) phase, S (Synthesis) phase and $G_2$ (Gap 2) phase, and divide at M (Mitosis) phase. Said "Gap 1" phase means that this phase locates behind said "M" phase and ahead of said "S" phase, and said "Gap 2" phase means that this phase locates behind said "S" phase and ahead of said "M" phase. At mitosis, chromosomes condense, attach to mitotic spindles and segregate in each cell. Colhitin or its derivative colcemid arrest the cells at mitosis, whereby inhibiting the formation of mitotic spindles. Therefore, these agents are widely used for obtaining mitotic chromosomes. However, it is well known by those skilled in the art that it is often difficult to acquire chromosomes from cells which proliferate slowly, because they do not pass through mitosis. In addition, many of biological events go on during interphase such as chromosome breakage by irradiation. So several attempts have been done to obtain interphase chromosomes to overcome these problems. One of these is the technique of premature chromosome condensation (PCC).

Figure 2:
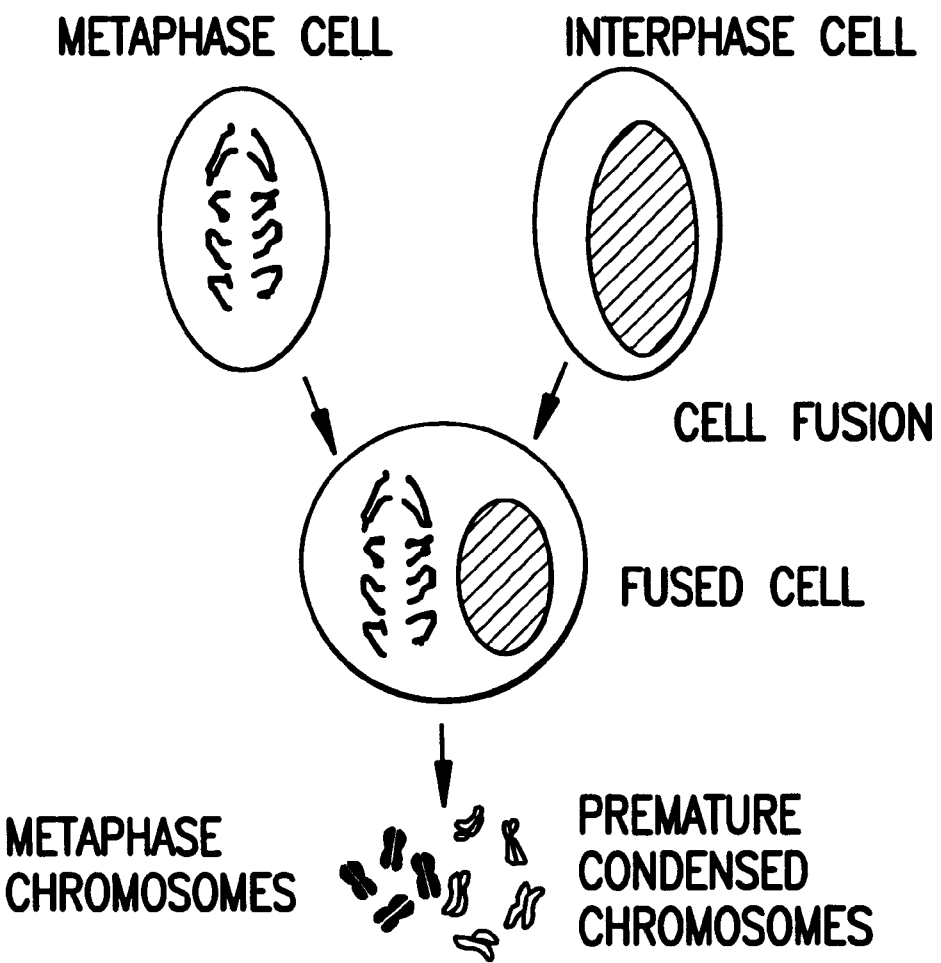
FIG. 2 illustrates the conventional PCC method by cell fusion.
Figure 3A:
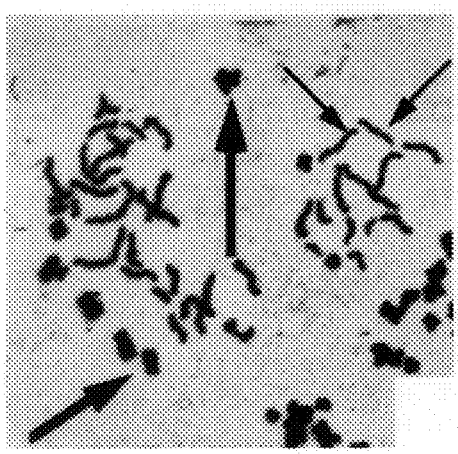
FIG. 3 shows a microphotograph (×1000) of prematurely condensed chromosomes obtained by conventional cell fusion method; (PCC)
Figure 3D:
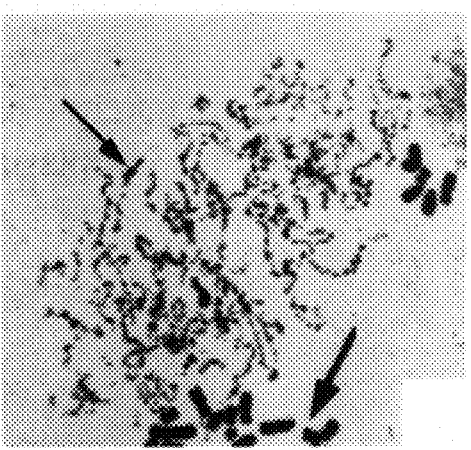
Figure 3B:
Figure 3E:
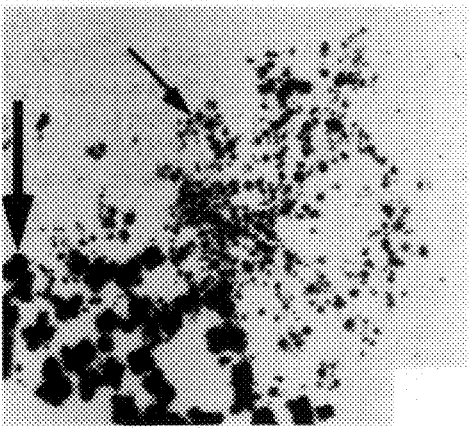
Figure 3C:
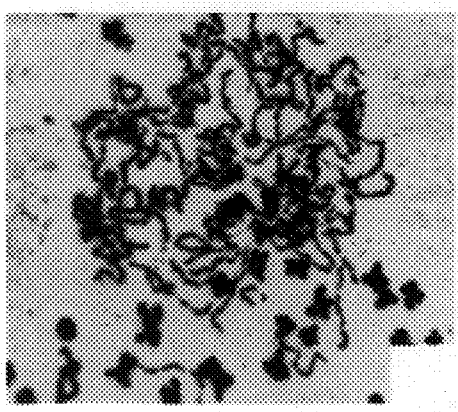
Figure 3F:
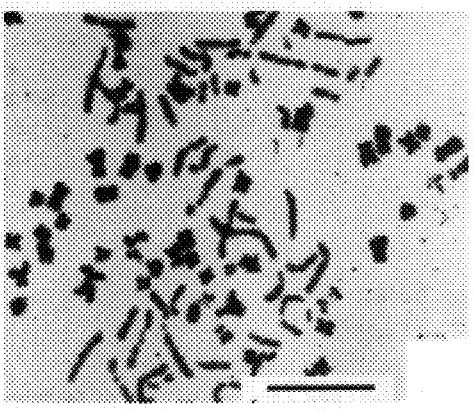

Referring to FIGS. 2 and 3 which are schematic showing of PCC by cell fusion method and the prematurely condensed chromosomes obtained by this technique, respectively. When the interphase cell is fused in mitotic cell, the interphase nucleus undergoes PCC (FIG. 2). Various kinds of PCC are shown in FIG. 3. Numerals 3-a and 3-b are $G_1$-PCC; well condensed but univalent chromosomes. Numeral 3-c is early S-PCC; decondensed and filamentous shape. Numerals 3-d and 3-e are S-PCC; a typical "pulverized" appearance. Numeral 3-f is $G_2$-PCC; well condensed and bivalent chromosomes identical with metaphase chromosomes. Small arrows indicate the chromosomes prematurely condensed by cell fusion, and large arrows indicate the metaphase chromosomes of inducer cells. Bar indicates 10 μm. This fusion method is very useful to obtain interphase chromosomes, but it is technically demanding: synchronize and arrest the inducer cells at mitosis, and fuse with-target cells. The efficiency of cell fusion is not so high. In addition, the chromosomes obtained by cell fusion are a mixture of those of inducer and target cells as shown in FIG. 3. Therefore, it makes it difficult to use this technique widely.

Figure 4:
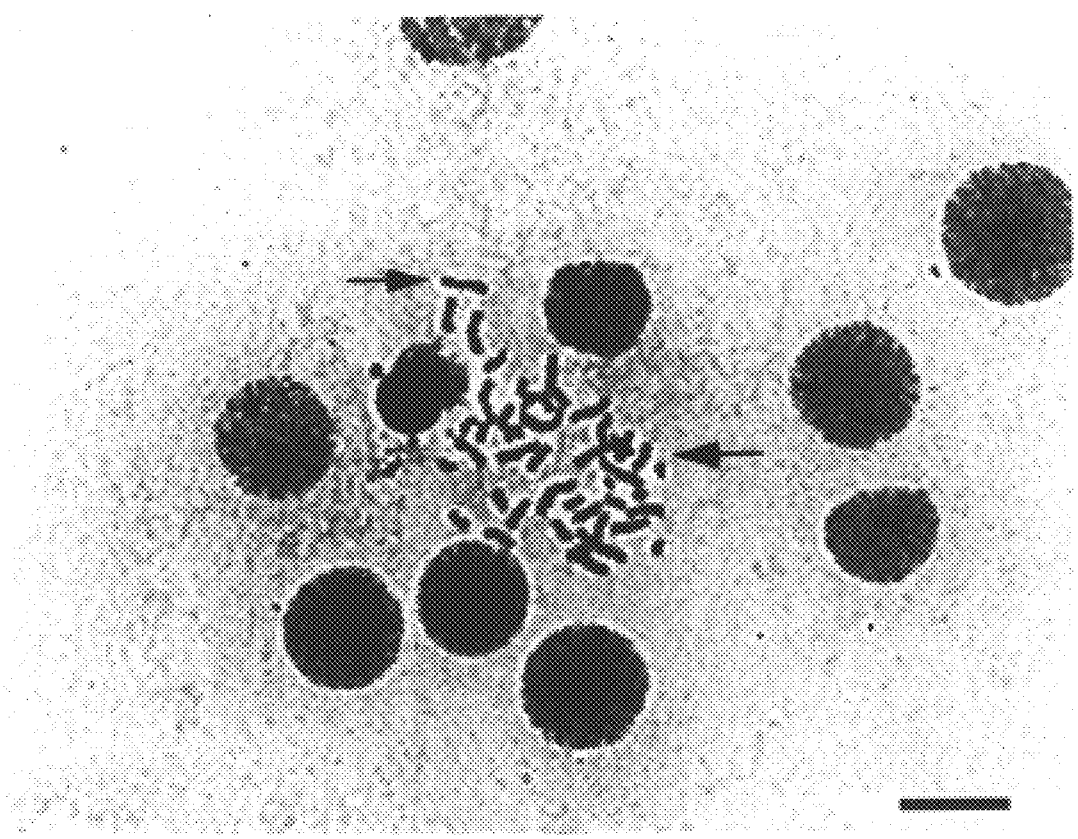
FIG. 4 shows a photomicrograph of metaphase chromosomes obtained after treatment with conventional colcemid method.
Figure 5A:
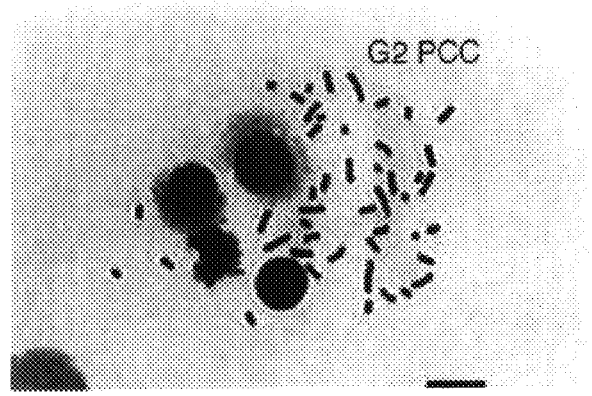
FIG. 5 shows the chromosomes prematurely condensed by okadaic acid of various concentration according to the present invention.
Figure 5B:
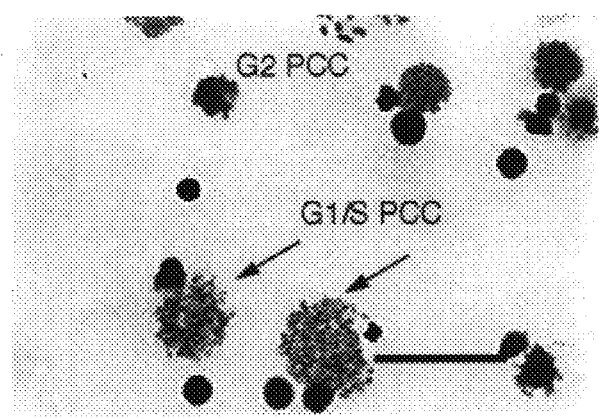
Figure 5C:
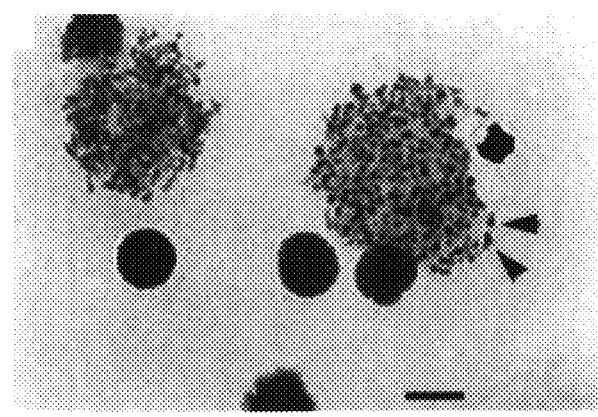
Figure 5D:
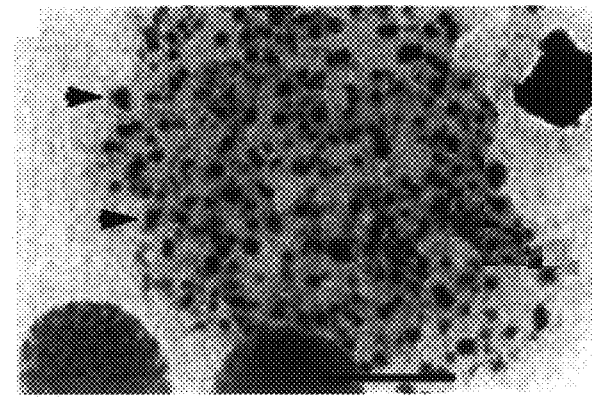

FIG. 4 shows metaphase chromosomes obtained after treatment with colcemid, as a control study.

Referring now to the agents used in the present invention. Okadaic acid, an agent extracted from a marine sponge Haricondria Okadai, is a specific inhibitor of serine/threonine protein phosphatases. Okadaic acid has a molecular weight (M.W.) of 805.2 and its agent structure is $C_{44}H_{68}O_{13}$. Okadaic acid ammonium salt ($C_{44}H_{67}O_{13}$-$NH_4$, M.W. 822.05) and 35-methyl okadaic acid ($C_{45}H_{70}O_{13}$, M.W. 819.04) are derivatives of okadaic acid, both show inhibitory effect on protein phosphatase as okadaic acid does. Calyculin A ($C_{50}H_{81}O_{15}P$, M.W. 1009.18) is another toxin obtained from a marine sponge Discodermia Calyx, which is also an inhibitor of protein phosphatases. Tautomycin ($C_{41}H_{66}O_{13}$, M.W. 766.97) is an antibiotic extracted from a soil bacteria Sterptomyces spiroverticillatus.. Cantharidine ($C_{10}H_{12}O_4$, M.W. 196.2) is an agent extracted from an erosive secretion of a blister beetle. Cantharidic acid ($C_{10}H_{14}O_5$, M.W. 214.2) and Endothal ($C_8H_{10}O_5$, M.W. 186.2) are derivatives of Cantharidine. These are also inhibitors of protein phosphatase as okadaic acid. All the agents presented here are specific inhibitor of serine/threonine protein phosphatases, especially of type 1 and type 2A protein phosphatases. In addition, all of these show cell permeability. All the agents except for okadaic acid ammonium salt were dissolved in 100% ethanol, methanol or dimethyl-sulfoxide (DMSO) to make a stock solution of 1 mM concentration (okadaic acid, 35-methyl okadaic acid, calyculin A or tautomycin) or 100 mM (cantharidine, cantharidic acid or endothal). Okadaic acid ammonium salt was dissolved in water to make a stock solution. of 1 mM concentration.

As used herein "protein phosphatase" or more specifically "serine/threonine protein phosphatase", refers to the enzymes that catalyze dephosphorylation of phosphorylated protein, especially of dephosphorylation of phosphorylated serine and/or phosphorylated threonine amino acid residues of protein. These enzymes are generally classified into 4 types, namely, type 1, type 2A, type 2B and type 2C according to their subunit structure, their dependencies of metal ion for their catalyzing activity, or other factors.

As used herein "inhibitor of protein phosphatase", refer to the agents that inhibit the catalyzation of the protein dephosphorylation by said protein phosphatases.

By using protein phosphatase inhibitors listed above as an inducer of PCC, the present invention provides a new way to generate chromosomes condensed prematurely from interphase nuclei, easily and more quickly than the conventional cell fusion method.

Referring now to FIG. 5 which shows the prematurly condensed chromosomes generated by the present invention using 100 nM okadaic acid (as final concentration). Hereafter, the concentration of each agent used in the present study indicates the final concentration in the culture medium, so far not specified. Herein used "$G_1$/S-PCC", refers to the terms combined the $G_1$-PCC and S-PCC. Although $G_1$-PCC and S-PCC are different from each other in strict meaning, the frequency of $G_1$-PCC is much less than that of S-PCC and it is difficult to distinguish them practically. So we scored both types of PCC together and termed as "$G_1$/S-PCC". When the human peripheral blood lymphocytes were affected with this agent, the cells underwent PCC at any phase of cell cycle. FIG. 5-a shows $G_2$-PCC, which shape is the same as that of metaphase chromosomes obtained after treatment of colcemid (Bar indicates 10 μm). FIG. 5-b shows $G_1$/S-PCC (indicated by arrows) and $G_2$-PCC (Bar indicates 50 μm). $G_1$/S-PCC shows a typical form "pulverized appearance" as shown in FIGS. 5-c and its magnified picture, 5-d. $G_1$/S-PCC is composed of thick and thin parts of chromatin. It is thought that the former corresponds to replicated chromosomes, whereas the latter corresponds to unreplicated chromatins. Arrowheads indicate the thick portion in $G_1$/S-PCC (Bars indicate 10 μm). So the phenomenon studied here is actually PCC. Preferred embodiment is that this technique requires only addition of agent in the culture medium. It does not require any laborious procedure; synchronizing and collecting large amounts of mitotic cells followed by fusion with target cells. Furthermore, the present invention is thus very simple.

Table 1 shows the dose response of PCC induced by okadaic acid in various types of mammalian cells. As human cells, Phytohemaggulitin-P (PHA-P) stimulated human peripheral blood lymphocytes from two healthy donors, established cell line AT(L)5KY and AT(L)6KY were used. Whereas as mouse cells, Concanavalin-A (Con-A) or Lipopolysaccharide (LPS) stimulated mouse splenocytes and established cell line Ba/F3 were used. As used herein "PHA-P", "Con-A" and "LPS" are mitogens usually used for stimulate the lymphocytes, that is well known by those skilled in the art. These cells were treated with okadaic acid of which concentration varies from 1 nM to 100 nM. After 2 hours' exposure, cells were harvested and subjected to hypotonic treatment. Then cells were fixed with methanol:acetic acid (3:1) and chromosome spreads were obtained, which is well known by those skilled in the art. $G_1$/S-PCC or $G_2$-PCC was scored and frequencies (putted in parentheses as a percentage) were obtained. As a control study, cells were treated with colcemid for 2 hours to generate metaphase chromosomes. The same hypotonic treatment and fixation were done. In the case of the concentration of okadaic acid is lower than 10 nM, $G_2$-PCC was solely induced. In contrast, 100 nM okadaic acid induced both $G_1$/S-PCC and $G_2$-PCC effectively. Furthermore, the frequency of $G_1$/S-PCC and $G_2$-PCC were much higher than that of metaphase chromosomes obtained by the conventional colcemid treatment.

FIG. 6 shows the graphical representation of the result shown in above Table 1. The frequencies of PCC or metaphase chromosomes are shown as an average number of each species, human and mouse cells. With respect to colcemid treatment, $G_2$-PCC should be interpreted as metaphase chromosomes. As clearly shown in the FIG. 6, 1 nM or 10 nM okadaic acid favor to induce $G_2$-PCC solely in human and mouse cells. In contrast, 100 nM okadaic acid can induce both $G_1$/S-PCC and $G_2$-PCC in human and mouse cells.

Table 2 shows the dose response of PCC induced by calyculin A in the same kinds of mammalian cells used in the experiment with okadaic acid.

TABLE 1

| Sample Name | Treatment | | Intrerphase Cell (%) | G1/S PCC (%) | G2/M PCC (%) | Total Number |
|---|---|---|---|---|---|---|
| Human | | | | | | |
| Human lymphocyte #1 | Colcemid | | 364 (97.3) | | 10 (2.6) | 374 |
| | Okadaic acid | 1 nM | 389 (97.7) | 0 (0.0) | 9 (2.3) | 398 |
| | Okadaic acid | 10 nM | 500 (97.2) | 1 (0.2) | 13 (2.5) | 514 |
| | Okadaic acid | 100 nM | 123 (56.7) | 54 (24.9) | 40 (18.6) | 217 |
| Human lymphocytes #2 | Colcemid | | 622 (95.8) | | 27 (4.2) | 649 |
| | Okadaic acid | 1 nM | 480 (98.0) | 0 (0.0) | 10 (2.0) | 490 |
| | Okadaic acid | 10 nM | 773 (98.6) | 0 (0.0) | 11 (1.4) | 784 |
| | Okadaic acid | 100 nM | 77 (59.7) | 39 (38.2) | 10 (8.0) | 126 |
| AT(L)5KY | Colcemid | | 381 (97.9) | | 8 (2.1) | 389 |
| | Okadaic acid | 1 nM | 493 (97.8) | 0 (0.0) | 11 (2.2) | 504 |
| | Okadaic acid | 10 nM | 347 (95.8) | 0 (0.0) | 15 (4.1) | 362 |
| | Okadaic acid | 100 nM | 89 (50.6) | 66 (37.5) | 21 (11.9) | 176 |
| AT(L)6KY | Colcemid | | 282 (98.6) | | 4 (1.4) | 286 |
| | Okadaic acid | 1 nM | 453 (98.6) | 0 (0.0) | 6 (1.4) | 469 |
| | Okadaic acid | 10 nM | 394 (96.8) | 0 (0.0) | 13 (3.2) | 407 |
| | Okadaic acid | 100 nM | 179 (60.1) | 97 (32.6) | 22 (7.4) | 298 |
| Mouse | | | | | | |
| Mouse lymphocyte (Con A) | Colcemid | | 264 (93.3) | | 19 (6.7) | 283 |
| | Okadaic acid | 1 nM | 280 (96.9) | 0 (0.0) | 9 (3.1) | 289 |
| | Okadaic acid | 10 nM | 196 (96.6) | 0 (0.0) | 7 (3.4) | 203 |
| | Okadaic acid | 100 nM | 163 (88.5) | 6 (3.3) | 15 (8.2) | 184 |
| Mouse lymphocytes (LPS) | Colcemid | | 265 (88.0) | | 36 (12.0) | 301 |
| | Okadaic acid | 1 nM | 248 (94.7) | 0 (0.0) | 14 (5.3) | 262 |
| | Okadaic acid | 10 nM | 148 (93.7) | 0 (0.0) | 10 (6.3) | 158 |
| | Okadaic acid | 100 nM | 116 (78.4) | 17 (11.5) | 15 (10.1) | 148 |
| Ba/F3 | Colcemid | | 261 (92.2) | | 22 (7.8) | 283 |
| | Okadaic acid | 1 nM | 254 (92.4) | 0 (0.0) | 21 (7.6) | 275 |
| | Okadaic acid | 10 nM | 303 (92.4) | 0 (0.0) | 25 (7.6) | 328 |
| | Okadaic acid | 100 nM | 138 (88.5) | 2 (1.3) | 16 (10.3) | 156 |

TABLE 2

| Sample Name | Treatment | | Interphase Cell (%) | G1/S PCC (%) | G2/M PCC (%) | Total Number |
|---|---|---|---|---|---|---|
| Human | | | | | | |
| Lymphocytes | Colcemid | | 364 (97.3) | | 10 (2.6) | 374 |
| | Calc A | 1 nM | 424 (98.4) | 0 (0.0) | 7 (1.6) | 431 |
| | Calc A | 10 nM | 393 (94.6) | 11 (2.7) | 11 (2.7) | 415 |
| | Calc A | 100 nM | 89 (61.0) | 30 (20.5) | 27 (18.5) | 146 |
| AT(L)5KY | Colcemid | | 381 (97.9) | | 8 (2.1) | 389 |
| | Calc A | 1 nM | 331 (96.2) | 0 (0.0) | 13 (3.8) | 344 |
| | Calc A | 10 nM | 101 (54.6) | 65 (35.1) | 19 (10.3) | 185 |
| | Calc A | 100 nM | 27 (26.2) | 50 (48.5) | 26 (25.2) | 103 |
| AT(L)6KY | Colcemid | | 282 (98.6) | | 4 (1.4) | 286 |
| | Calc A | 1 nM | 251 (97.6) | 0 (0.0) | 6 (2.3) | 257 |

TABLE 2-continued

| Sample Name | Treatment | | Interphase Cell (%) | G1/S PCC (%) | G2/M PCC (%) | Total Number |
|---|---|---|---|---|---|---|
| | Calc A | 10 nM | 144 (72.0) | 39 (19.5) | 17 (8.5) | 200 |
| | Calc A | 100 nM | 45 (37.8) | 49 (41.1) | 25 (21.1) | 119 |
| Mouse | | | | | | |
| Lymphocytes (Con A) | | Colcemid | 264 (93.3) | | 19 (6.7) | 283 |
| | Calc A | 1 nM | 376 (95.2) | 1 (0.2) | 18 (4.6) | 395 |
| | Calc A | 10 nM | 9 (10.1) | 48 (57.8) | 26 (31.3) | 83 |
| | Calc A | 100 nM | — | — | — | — |
| Lymphocytes (LPS) | | Colcemid | 265 (88.0) | | 36 (12.0) | 301 |
| | Calc A | 1 nM | 217 (94.8) | 0 (0.0) | 12 (5.2) | 229 |
| | Calc A | 10 nM | 25 (20.8) | 45 (37.5) | 50 (41.6) | 120 |
| | Calc A | 100 nM | — | — | — | — |
| Ba/F3 | | Colcemid | 261 (92.2) | | 22 (7.8) | 283 |
| | Calc A | 1 nM | 197 (89.9) | 7 (3.2) | 15 (6.8) | 219 |
| | Calc A | 10 nM | 0 (0.0) | 111 (75.0) | 37 (25.0) | 148 |
| | Calc A | 100 nM | 1 (0.8) | 69 (59.4) | 46 (39.7) | 116 |

These cells were treated with calyculin A of which concentration varies from 1 nM -to 100 nM. After 2 hours' exposure, PCC were obtained as described above. Control study was also done using colcemid. The appearances of PCC were identical to those induced by okadaic acid. Therefore I do not present photographs hereafter. When the concentration of calyculin A is I nM, $G_2$-PCC was solely induced. In contrast, more than 10 nM calyculin A induced both $G_1$/S-PCC and $G_2$-PCC effectively. As same as okadaic acid, frequency of both $G_1$/S-PCC and $G_2$-PCC induced by more than 10 nM calyculin A were much more effective than that of metaphase chromosomes obtained by the conventional colcemid treatment. As to mouse splenocytes, calyculin A showed much higher cell toxicity than okadaic acid, thus resulted in loss of cells during culture. Therefore we omitted the experiment using 100 nM calyculin A for these cell types. Even at 10 nM concentration, calyculin A exerted PCC effectively.

FIG. 7 shows the graphical representation of the result shown in above Table 2. The frequencies of PCC or metaphase chromosomes are shown as an average number of each species, human and mouse. In the case of colcemid treatment, $G_2$-PCC should be interpreted as metaphase chromosomes. As clearly shown, 1 nM calyculin A favor to induce $G_2$-PCC solely in human and mouse cells. In contrast, more than 10 nM calyculin A can induce both $G_1$/S-PCC and $G_2$-PCC in human and mouse cells.

According to the experiments described above, it was found that both okadaic acid and calyculin A could induce PCC in mammalian cells at any time of cell cycle. These agents have a common feature as a specific inhibitor of protein phosphatases, more specifically type 1 and type 2A of serine/threonine protein phosphatases But these agent structures are somewhat different from each other. So the PCC induced by these agents is thought to be contributed by the inhibitory effect of protein phosphatase. Therefore we investigated the PCC inducibility using other inhibitors of protein phosphatase; okadaic acid ammonium salt, 35-methyl okadaic acid, tautomycin, cantharidine, cantharidic acid and endothal. The profiles of these agents were shown above.

Now referring to Table 3, which shows the result of the frequency of PCC obtained after treating of this agent in human peripheral blood lymphocytes. Cells were stimulated and cultured as done in the experiment using okadaic acid or calyculin A. Cells were treated with each agent for 2 hours, then PCC were obtained as described above.

TABLE 3

| Sample Name | Treatment | | Interphase Cell (%) | G1/S PCC (%) | G2/M PCC (%) | Total Number |
|---|---|---|---|---|---|---|
| Human | | | | | | |
| Human Lymphocytes | | Colcemid | 344 (97.7) | | 8 (2.3) | 352 |
| | Okadaic acid Ammonium salt | 1 nM | 244 (96.8) | 0 (0.0) | 8 (3.2) | 252 |
| | Okadaic acid Ammonium salt | 10 nM | 259 (96.6) | 0 (0.0) | 9 (3.4) | 268 |
| | Okadaic acid Ammonium salt | 100 nM | 156 (57.1) | 83 (30.4) | 34 (12.5) | 273 |
| Human Lymphocytes | | Colcemid | 363 (97.0) | | 11 (3.0) | 374 |
| | 35-methyl okadaic acid | 1 nM | 277 (96.8) | 0 (0.0) | 9 (3.2) | 286 |
| | 35-methyl okadaic acid | 10 nM | 263 (96.5) | 0 (0.0) | 10 (3.5) | 273 |
| | 35-methyl okadaic acid | 100 nM | 161 (63.1) | 62 (24.3) | 32 (12.6) | 255 |
| Human Lymphocytes | | Colcemid | 364 (97.3) | | 10 (2.6) | 374 |
| | Cantharidin | 500 nM | 266 (97.5) | 0 (0.0) | 7 (2.5) | 273 |
| | Cantharidin | 5 uM | 213 (92.0) | 12 (5.3) | 7 (2.7) | 232 |
| | Cantharidin | 50 uM | 260 (78.8) | 61 (18.5) | 9 (2.7) | 330 |
| Human Lymphocytes | | Colcemid | 381 (97.9) | | 8 (2.1) | 389 |
| | Cantharidic acid | 500 nM | 257 (97.5) | 0 (0.0) | 7 (2.5) | 264 |
| | Cantharidic acid | 5 uM | 201 (91.0) | 13 (6.0) | 7 (3.0) | 221 |
| | Cantharidic acid | 50 uM | 221 (85.3) | 29 (11.2) | 9 (3.5) | 259 |

TABLE 3-continued

| Sample Name | Treatment | | Interphase Cell (%) | G1/S PCC (%) | G2/M PCC (%) | Total Number |
|---|---|---|---|---|---|---|
| Human Lymphocytes | | Colcemid | 364 (97.3) | | 10 (2.6) | 374 |
| | Endothal | 500 nM | 268 (98.2) | 0 (0.0) | 5 (1.8) | 273 |
| | Endothal | 5 uM | 262 (97.8) | 0 (0.0) | 8 (2.2) | 268 |
| | Endothal | 50 uM | 223 (94.6) | 6 (2.5) | 7 (2.9) | 236 |
| Human Lymphocytes | | Colcemid | 282 (98.6) | | 4 (1.4) | 286 |
| | Tautomycin | 100 nM | 236 (97.4) | 0 (0.0) | 7 (2.5) | 243 |
| | Tautomycin | 1 uM | 270 (95.5) | 3 (1.0) | 10 (3.5) | 283 |
| | Tautomycin | 10 uM | 200 (84) | 28 (11.8) | 10 (4.2) | 238 |

Okadaic acid ammonium salt or 35-methyl okadaic acid could induce $G_1$/S-PCC and $G_2$-PCC at their concentration was 100 nM. At 1 nM or 10 nM of these agents, $G_2$-PCC was solely induced. These findings were the same as in the case of okadaic acid. So the effect of these 3 agents is thought to be identical.

Cantharidine or cantharidic acid could induce $G_1$/S-PCC and $G_2$-PCC at their concentration higher than 5 $\mu$M, and $G_2$-PCC only was induced at 500 nM these agents. Canthari-dine or cantharidic acid were required to have the higher concentration to induce PCC than that of okadaic acid. Inhibitory dose ($IC_{50}$) of cantharidine or cantharidic acid for protein phosphatase is higher than that of okadaic acid. Probably, this is the one reason for explaining the differences of the dose required.

Endothal also could cause $G_1$/S-PCC and $G_2$-PCC at 50 $\mu$M. However, it could induce $G_2$-PCC solely at less than 5 $\mu$M. Furthermore, the frequency of $G_1$/S-PCC and $G_2$-PCC at 50 $\mu$M endothal were less than those induced with cantharidine or cantharidic acid at same concentration. Endothal can inhibit protein phosphatase partially, whereas cantharidine and cantharidic acid can do it almost completely. Probably, this makes for the differences between their inducibility of PCC.

Tautomycin could cause $G_1$/S-PCC and $G_2$-PCC at more than 1 $\mu$M, whereas it could induce $G_2$-PCC solely at 100 nM.

Table 4, which shows the result of the frequency of PCC obtained after the same experiment shown in Table 3 but in human established cell line

TABLE 4

AT(L)5KY.

| Sample Name | Treatment | | Interphase Cell (%) | G1/S PCC (%) | G2/M PCC (%) | Total Number |
|---|---|---|---|---|---|---|
| Human | | | | | | |
| Human AT(L)5KY | | Colcemid | 361 (96.5) | | 13 (3.5) | 374 |
| | Okadaic acid Ammonium salt | 1 nM | 244 (96.2)) | 0 (0.0) | 10 (3.8) | 254 |
| | Okadaic acid Ammonium salt | 10 nM | 239 (95.8) | 0 (0.0) | 11 (4.2) | 250 |
| | Okadaic acid Ammonium salt | 100 nM | 126 (47.9) | 94 (35.8) | 43 (16.3) | 263 |
| Human AT(L)5KY | | Colcemid | 370 (96.5) | | 13 (3.5) | 383 |
| | 35-methyl okadaic acid | 1 nM | 257 (96.0) | 0 (0.0) | 11 (4.0) | 268 |
| | 35-methyl okadaic acid | 10 nM | 263 (96.1) | 0 (0.0) | 10 (3.9) | 273 |
| | 35-methyl okadaic acid | 100 nM | 119 (48.6) | 89 (36.1) | 38 (15.3) | 246 |
| Human AT(L)5KY | | Colcemid | 357 (96.9) | | 11 (3.1) | 368 |
| | Cantharidin | 500 nM | 300 (96.2) | 0 (0.0) | 12 (3.8) | 312 |
| | Cantharidin | 5 uM | 175 (81.0) | 22 (10.2) | 19 (8.8) | 216 |
| | Cantharidin | 50 uM | 30 (18.3) | 111 (67.7) | 23 (14.0) | 164 |
| Human AT(L)5KY | | Colcemid | 346 (97.0) | | 10 (3.0) | 356 |
| | Cantharidic acid | 500 nM | 271 (96.4) | 0 (0.0) | 10 (3.6) | 281 |
| | Cantharidic acid | 5 uM | 197 (85.6) | 22 (9.6) | 11 (4.8) | 230 |
| | Cantharidic acid | 50 uM | 39 (26.5) | 88 (59.9) | 20 (13.6) | 147 |
| Human AT(L)5KY | | Colcemid | 349 (97.5) | | 9 (2.5) | 358 |
| | Endothal | 500 nM | 289 (97.3) | 0 (0.0) | 8 (2.7) | 297 |
| | Endothal | 5 uM | 298 (96.8) | 0 (0.0) | 10 (3.2) | 308 |
| | Endothal | 50 uM | 179 (92.6) | 7 (3.7) | 7 (3.7) | 193 |
| Human AT(L)5KY | | Colcemid | 295 (97.7) | | 7 (2.3) | 302 |
| | Tautomycin | 100 nM | 232 (95.8) | 0 (0.0) | 10 (4.1) | 242 |
| | Tautomycin | 1 uM | 217 (93.9) | 3 (1.3) | 11 (4.8) | 231 |
| | Tautomycin | 10 uM | 142 (66.4) | 56 (26.3) | 16 (7.4) | 214 |

As easily recognized, they showed the same inclination as obtained from human peripheral blood lymphocytes. So these phenomena are in common and not depend on cell types. To make brevity, graphical representations of Table 3 and 4 are not shown.

In conclusion, we could induce PCC at any phase of cell cycle in mammalian cells (human and mouse cells were investigated in the present invention), using several kinds of inhibitors of protein phosphatases. All of agents used herein could induce PCC in all kinds of cells used here. The effective dose to induce PCC were different for each agent, probably due to the differences in cell permeability, the degradation in cells, or the sensitivity of cells to each agent. All of the agents used herein have cell permeability, this allows one to use these agents to induce PCC much more simply as accomplished by the present invention. The agent having inhibitory effect of protein phosphates but not cell permeability (such as microcystin-LR), could not induce PCC at all after addition it into the culture medium (data not shown). Therefore, besides the inhibitory effect of protein phosphatase, the agents should have cell permeability. Otherwise, a laborious technique should be required to inject an agent into cells, such as micro-injection or cell portion technique. It is noteworthy that the method in the present invention gives the way to generate the chromosomes from interphase nuclei, and that it permit one to investigate the genetically events occur in the interphase nuclei. Furthermore the method in the present invention is much more simple than the known cell fusion method, which only requires the addition of agents into the culture medium, which leads to induction of PCC quickly, easily and with highly reproducibility. Thus the method in the present invention will provide a way to develop an assay or a diagnosis kit of analyze the chromosomes of many fields including clinical, medical, zoology, veterinary medicine, fisheries, botany or agriculture.

Although the preferred embodiments of the present invention have been explained, in detail, herein above, the present invention should not be limited to these embodiments alone, but various modifications and changes, including an improvement or a discovery of new agents that have inhibitory effect of protein phosphatase with cell permeability, can be made thereto without departing from the scope of the invention defined in the appended claims.

Thus the present invention provides an agent for inducing premature chromosome condensation (PCC) and which acts as an inhibitor of protein phosphatases which comprises at least one of okadaic acid, calyculin A, okadaic acid ammonium salt, 35-methyl okadaic acid, tautomycin, cantharidine, cantharidic acid or endothal dissolved in predetermined solvent.

The present invention also provides an agent for inducing PCC and which acts as an inhibitor of protein phosphatases and which comprises at least one of okadaic acid, okadaic acid ammonium salt, 35-methyl okadaic acid, calyculin A, tautomycin, cantharidine, cantharidic acid and endothal, dissolved in a predetermined solvent and for diagnostic use.

The agent may be effective at any stage of the cell cycle: G1 (Gap 1 phase), S (DNA synthesis phase), G2 (Gap 2 phase) or M (mitosis phase).

The agent may comprise okadaic acid or calyculin A.

The present invention also provides use of at least one of okadaic acid, okadaic acid ammonium salt, 35-methyl okadaic acid, calyculin A, tautomycin, cantharidine, cantharidic acid or endothal dissolved in a predetermined solvent as an agent to inhibit protein phosphatases for the purpose of inducing PCC.

In such use, the agent may comprise okadaic acid or calyculin A.

The present invention also provides use of at least one of okadaic acid, okadaic acid ammonium salt. 35-methyl okadaic acid, calyculin A, tautomycin, cantharidine, cantharidic acid and endothal which act as inhibitors of protein phosphatases and induce PCC, for the manufacture of a diagnostic agent.

Use may be of okadaic acid or calyculin A.

The present invention also provides a method for generating chromosomes by PCC which comprises treating proliferating cells with an agent which inhibits protein phosphatases and induces PCC which agent comprises at least one of okadaic acids calyculin A, okadaic acid ammonium salt, 35- methyl okadaic acid, tautomycin, cantharidine, cantharidic acid or endothal dissolved in predetermined solvent.

In such a method the agent may comprise okadaic acid or calyculin A.

In such a method the final concentration of okadaic acid or calyculin A may be in the range of 1 to 100 nM.

In such a method the final concentration of okadaic acid may be either (i) higher than 100 nM and such that it can generate G1 phase, S phase or G2 phase PCC; or (ii) in the range of 1 to 10 nM and such that it can generate G2 phase PCC.

In such a method the final concentration of calyculin A may be either (i) higher than 10 nM and such that it can generate G1 phase, S phase or G2 phase PCC; or (ii) 1 nM and able to generate G2 phase PCC.

In such a method the agent may comprise either okadaic acid ammonium salt or 35-methyl okadaic acid.

In such a method the final concentration of the okadaic acid ammonium salt or 35-methyl okadaic acid may be 1 to 100 nM.

In such a method the final concentration of the okadaic acid ammonium sale or 35-methyl okadaic acid may be either (i) higher than 100 nM and such that it can generate G1 phase, S phase or G2 phase PCC; or (ii) in the range of 1 to 10 nM and such that it can generate G2 phase PCC.

In such a method the agent may comprise tautomycin.

In such a method the final concentration of tautomycin may be 100 nM to 10 $\mu$M.

In such a method the final concentration of tautomycin may be either (i) higher than 1 $\mu$M and such that it can generate G1 phase, S phase or G2 phase PCC; or (ii) 100 nM such that it can generate G2 phase PCC.

In such a method the agent may comprise either cantharidine, cantharidic acid or endothal.

In such a method the final concentration of cantharidine, cantharidic acid or endothal may be 500 nM to 50 $\mu$M.

In such a method the final concentration of cantharidine, cantharidic acid or endothal may be either (i) higher than 5 $\mu$M and such that it can generate G1 phase, S phase or G2 phase PCC; or (ii) 500 nM such that it can generate G2 phase PCC.

The agents provided may be for chromosomal analysis of human cells for clinical or medical purposes.

The agents provided may be for chromosomal analysis of non-human cells.

The uses provided may be for chromosomal analysis of human cells for clinical or medical purposes.

The uses provided may be for chromosomal analysis of non-human cells.

The methods provided may be for chromosomal analysis of human cells for clinical or medical purposes.

The methods provided may be for chromosomal analysis of non-human cells.

The present invention also provides assays or diagnostic kits or reagents comprising an agent as above.

What we claim is:

1. A method of generating condensed chromosomes by premature chromosome condensation (PCC), which comprises treating proliferating cells with an inhibitor of protein phosphatases, which is a composition, comprising calyculin A dissolved in a solvent.

2. The method of claim 1, wherein said solvent is selected from the group consisting of methanol, ethanol, and dimethyl sulfoxide.

3. The method of claim 1, wherein said proliferating cells are human cells.

4. The method of claim 1, wherein said proliferating cells are animal cells.

5. A method of generating condensed chromosomes by premature chromosome condensation, which comprises treating proliferating cells with an inhibitor of protein phosphatases, which is calyculin A.

6. The method of claim 5, wherein a final concentration of calyculin A is from 1 to 100 nM.

7. The method of claim 5, wherein said proliferating cells are human cells.

8. The method of claim 5, wherein said proliferating cells are animal cells.

9. A method of analyzing human cell chromosomes by causing premature chromosome condensation, which comprises:
   a) applying an effective amount of a composition to human cells, thereby causing premature chromosome condensation; and
   b) evaluating the chromosomes treated in step a); wherein said composition comprises calyculin A dissolved in a solvent selected from the group consisting of methanol and ethanol.

10. A method of analyzing animal cell chromosomes by causing premature chromosome condensation, which comprises:
   a) applying an effective amount of a composition to animal cells, thereby causing premature chromosome condensation; and
   b) evaluating the chromosomes treated in step a); wherein said composition comprises calyculin A dissolved in a solvent selected from the group consisting of methanol and ethanol.

11. A diagnosis or assay kit for human cell chromosomes, comprising calyculin A and a solvent selected from the group consisting of methanol and ethanol.

12. A diagnosis or assay kit for animal cell chromosomes, comprising calyculin A, and a solvent selected from the group consisting of methanol and ethanol.

* * * * *